(12) United States Patent
Razink

(10) Patent No.: US 8,795,387 B1
(45) Date of Patent: Aug. 5, 2014

(54) PROSTHETIC WRIST

(76) Inventor: Matthew William Razink, Medford, WI (US)

( * ) Notice: Subject to any disclaimer, the term of this patent is extended or adjusted under 35 U.S.C. 154(b) by 231 days.

(21) Appl. No.: 13/398,788

(22) Filed: Feb. 16, 2012

(51) Int. Cl.
*A61F 2/58* (2006.01)

(52) U.S. Cl.
USPC .......................................................... 623/62

(58) Field of Classification Search
USPC .................... 623/48–49, 61–62, 65
See application file for complete search history.

(56) References Cited

U.S. PATENT DOCUMENTS

| | | |
|---|---|---|
| 2,749,557 A | 6/1956 | Riddle |
| 4,370,791 A | 2/1983 | Wilson |
| 4,636,221 A | 1/1987 | Kemp |
| 4,862,759 A | 9/1989 | Trevelyan et al. |
| 5,156,630 A | 10/1992 | Rappoport et al. |
| 5,464,444 A | 11/1995 | Garquharson et al. |
| 5,800,564 A | 9/1998 | Gelineau |
| 5,913,901 A | 6/1999 | Lacroix |
| 6,287,206 B1 * | 9/2001 | Stage ............................ 464/119 |
| 6,416,555 B1 * | 7/2002 | Dillenburg et al. ............. 623/65 |
| 7,097,666 B2 | 8/2006 | Curtis |
| 7,144,430 B2 | 12/2006 | Archer et al. |
| 7,318,366 B2 | 1/2008 | Lee et al. |
| 7,914,587 B2 * | 3/2011 | Archer et al. .................... 623/62 |
| 2004/0015240 A1 | 1/2004 | Archer et al. |
| 2007/0173955 A1 | 7/2007 | Archer et al. |
| 2007/0260328 A1 | 11/2007 | Bertels et al. |

\* cited by examiner

*Primary Examiner* — Bruce E Snow
(74) *Attorney, Agent, or Firm* — QuickPatents; Kevin Prince

(57) ABSTRACT

A prosthetic wrist for attaching between an arm prosthesis and a prosthetic accessory includes proximal section, a central section pivotally attached to the proximal section with a first joint, and a distal section pivotally attached to the central section with a second joint. The second joint includes a second pivot axis that is substantially orthogonal to and non-intersecting with the first pivot axis. The distal section further includes at a distal end thereof a terminal device attachment mechanism. The first and second joints each include a proximal portion, a distal portion, a pivot, and a lock mechanism adapted for allowing angular selection between the proximal and distal portions and locking thereof.

12 Claims, 4 Drawing Sheets

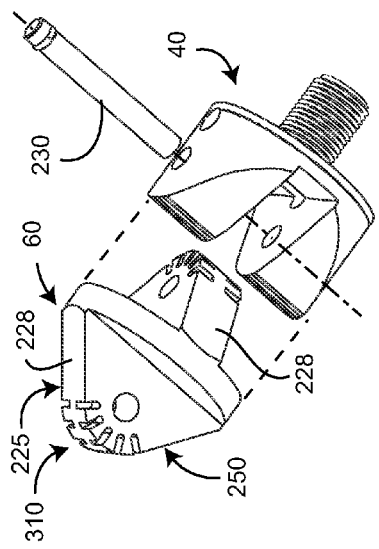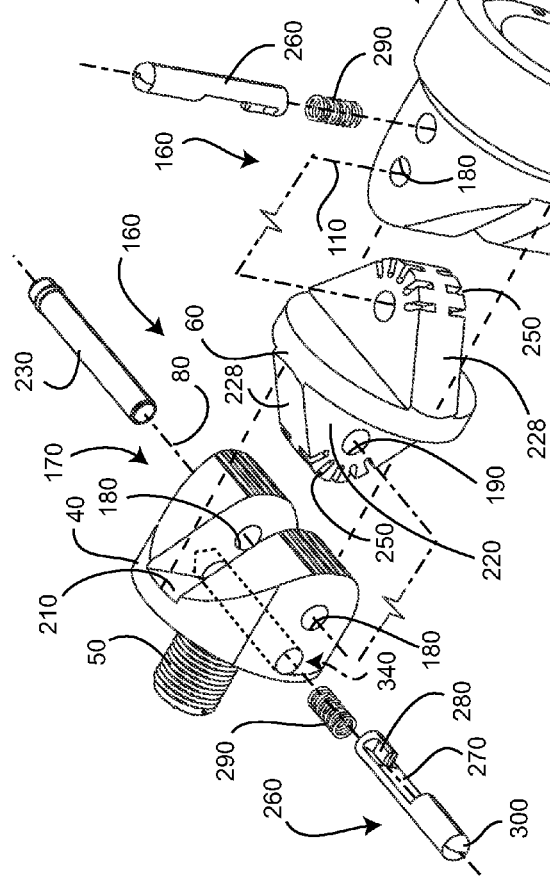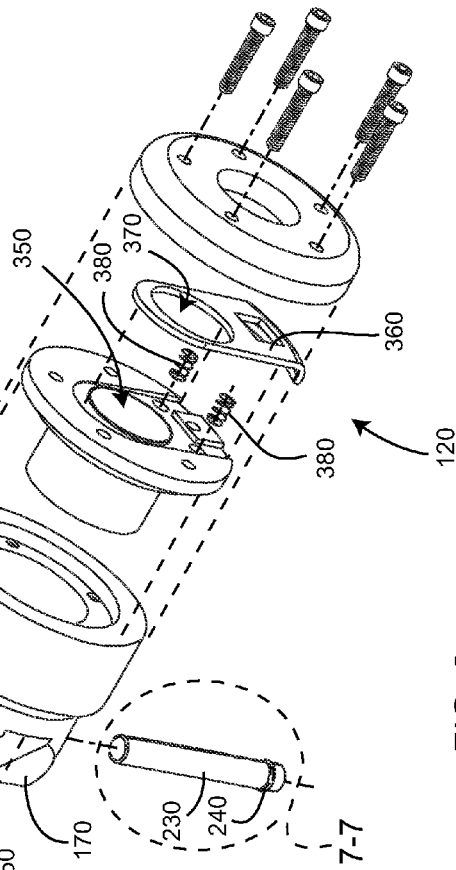

PROSTHETIC WRIST

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

This invention relates to prosthetic devices, and more particularly to a prosthetic wrist.

DISCUSSION OF RELATED ART

Prosthetic joints, such as wrist joints, are known in the prior art to include pivotable movement with respect to the arm prostheses only in one direction, that is, only around one axis. For example, US Patent Application 2007/0260328 to Bertels et al. on Nov. 8, 2007, teaches such a device, as does U.S. Pat. No. 2,749,557 to Riddle on Jun. 12, 1956. Such products typically have a means of locking a distal portion of the joint at a fixed angular position with respect to a proximal portion of the joint.

Frequently, however, it is desirable to move a terminal prosthetic accessory, such as an artificial hand or other tool, into an angle along a first axis and a second axis, and to lock such a device in any of a given number of fixed discrete pivotal positions. Therefore, there is a need for a device that allows for a user to fix an artificial hand or other such tool into an angle along a first and second axis, and to lock the device in such a desired position. Further, such a first and second axis are preferably offset and not in the same plane. Such a needed device, moreover, would be relatively simple for a one-handed user, for example, to disassemble, clean, and reassemble, requiring no tools. The present invention accomplishes these objectives.

SUMMARY OF THE INVENTION

The present device is a prosthetic wrist for attaching between an arm prosthesis attachment socket and a terminal device, such as a prosthetic hand or other prosthetic accessory. A proximal section has at a proximal end thereof an attachment post that is adapted for selective attachment with the prosthesis attachment socket. A central section is pivotally attached to the proximal section with a first joint. The first joint includes a first pivot axis. A distal section is pivotally attached to the central section with a second joint. The second joint includes a second pivot axis that is substantially orthogonal to and non-intersecting with the first pivot axis. The distal section further includes at a distal end thereof a terminal device attachment mechanism.

The first and second joints each include a proximal portion, a distal portion, a pivot, and a lock mechanism adapted for allowing angular selection between the proximal and distal portions and locking thereof. In one embodiment, the first and second joints each include a pair of fork extensions that each have a mutually-aligned aperture therethrough and that define a channel therebetween that has a floor. Further, the first and second joints each include a pivot arm that has an aperture therethrough, and a pivot pin insertable through the apertures of the fork extensions and pivot arm. As such, the pivot arm is pivotable within the channel about the pivot pin.

Preferably the proximal portion of the first joint and the distal portion of the second joint each include the fork extensions, and the distal portion of the first joint and the proximal portion of the second joint include the pivot arm, but other configurations could be utilized.

Each lock mechanism of each joint preferably includes a plurality of partially-transverse grooves in the peripheral surface of each pivot arm, and a locking pin that has a flat portion that is adapted to lie flush with the floor of the channel. The flat portion has a locking protrusion adapted to fit into any of the grooves of the pivot arm. A spring urges the locking protrusion towards the pivot arm. The locking pin includes an actuator depressed towards the fork extension to retract the locking protrusion away from the pivot arm, allowing the pivot arm to rotate about the pivot pin.

In use, with the wrist attached to the arm prosthesis attachment socket at the attachment post, and with the terminal device attached to the terminal device attachment mechanism, the angle between the proximal section and the central section may be manually set along the first pivot axis, and the angle between the central section and the distal section may be manually set along the second pivot axis.

The present invention is a device that allows for a user to fix an artificial hand or other such tool into an angle along a first and second axis, and to lock the device in such a desired position. Further, in the present device, the first and second axes are offset, that is, not in the same plane. The present invention is also relatively simple for a one-handed user, for example, to disassemble, clean, and reassemble, requiring no tools. Other features and advantages of the present invention will become apparent from the following more detailed description, taken in conjunction with the accompanying drawings, which illustrate, by way of example, the principles of the invention.

DESCRIPTION OF THE DRAWINGS

FIG. 6 is an exploded perspective view of the invention;

FIG. 7 is an exploded perspective view of a pivot pin of the invention; and

FIG. 8 is an exploded partial perspective view of the invention.

DETAILED DESCRIPTION OF THE PREFERRED EMBODIMENT

Figure 1:
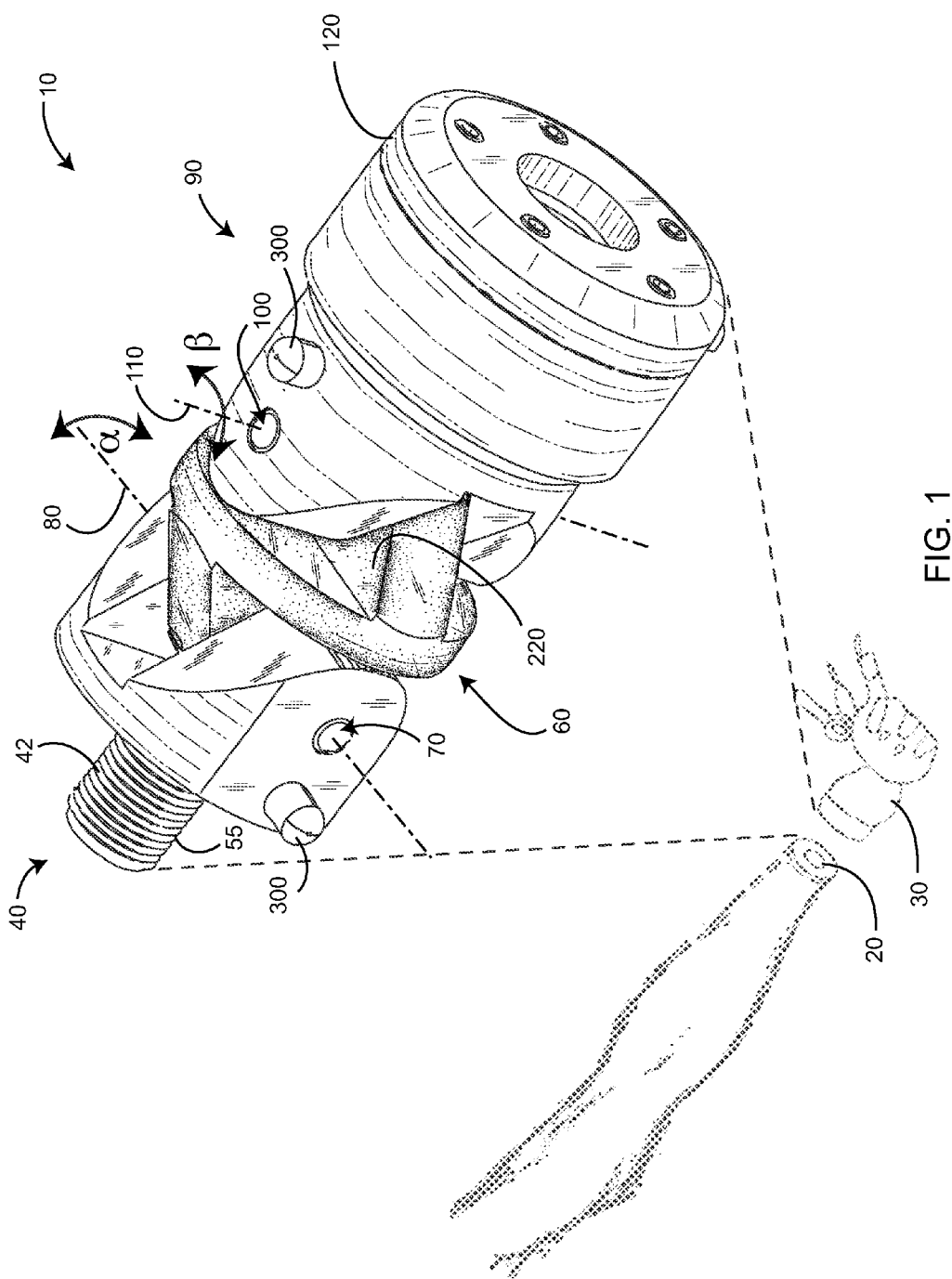
FIG. 1 is a perspective view of the invention.

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

FIGS. 1-3 and 6 illustrate a prosthetic wrist 10 for attaching between an arm prosthesis attachment socket 20 and a terminal device 30, such as a prosthetic hand or other prosthetic accessory.

A proximal section 40 has at a proximal end 42 thereof an attachment post 50 that is adapted for selective attachment with the prosthesis attachment socket 20. In one embodiment, the attachment post 50 includes a thread 55 for engaged with a threaded arm prosthesis attachment sock 20. Clearly, however, the attachment post 50 may include any other required attachment mechanism for attachment to the prosthesis attachment socket 20 based on the type of attachment socket 20 utilized.

Figure 2:
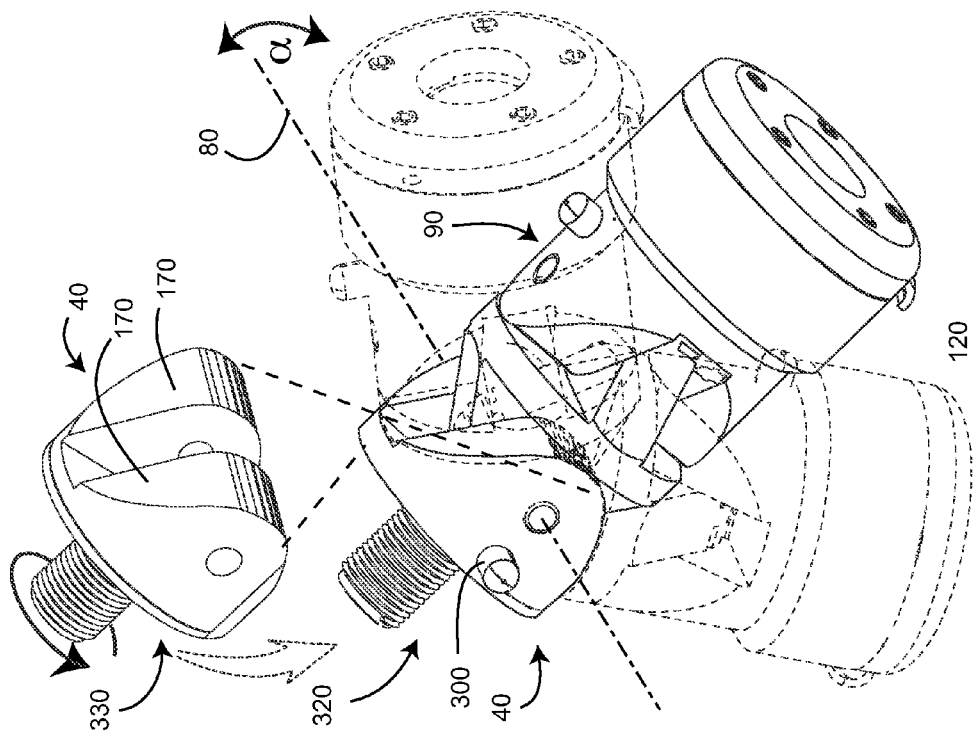
FIG. 2 is a perspective view of the invention, illustrating a proximal section thereof.
Figure 4:
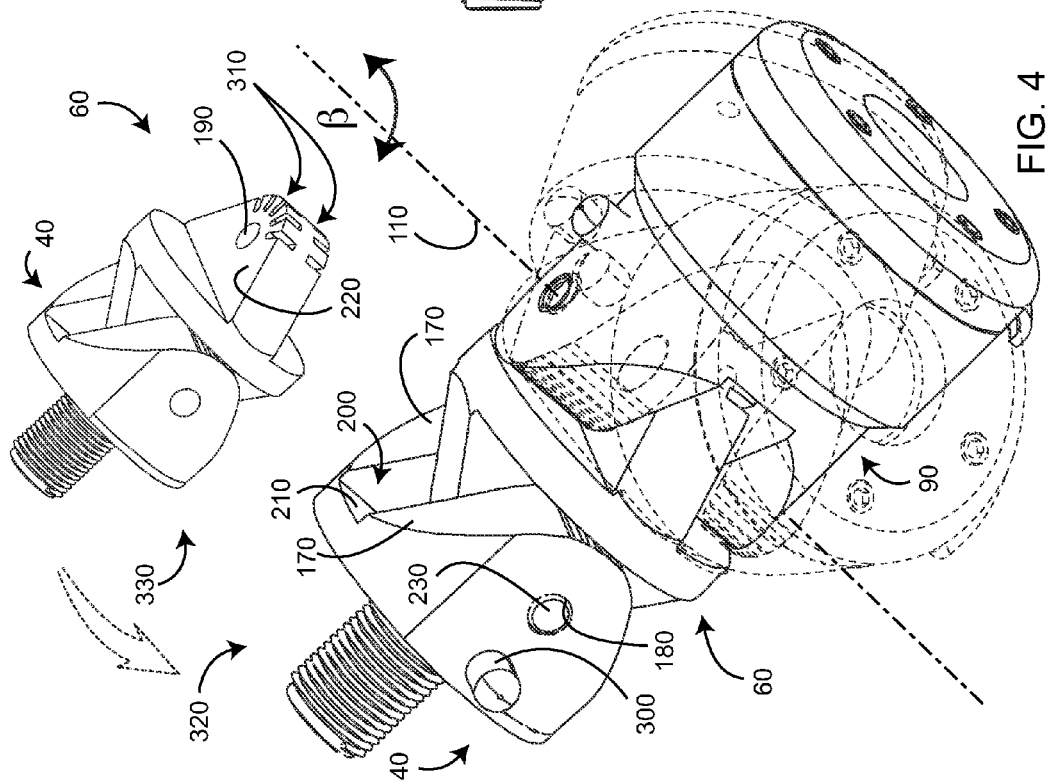
FIG. 4 is a perspective view of the invention, illustrating a central section thereof.

A central section (FIGS. 4-5) is pivotally attached to the proximal section with a first joint 70. The first joint 70 includes a first pivot axis 80 (FIG. 2).

A distal section 90 is pivotally attached to the central section 60 with a second joint 100. The second joint 100 includes a second pivot axis 110 (FIG. 4) that is substantially orthogonal to and non-intersecting with the first pivot axis 80. The distal section 90 further includes at a distal end 98 thereof a terminal device attachment mechanism 120.

The first and second joints 70,100 each include a proximal portion 130, a distal portion 140, a pivot 150, and a lock mechanism 160 adapted for allowing angular selection between the proximal and distal portions 130,140 and locking thereof.

In one embodiment, the first and second joints 70,100 each include a pair of fork extensions 170 that each have a mutually-aligned aperture 180 therethrough and that define a channel 200 therebetween that has a floor 210. Further, the first and second joints 70,100 each include a pivot arm 220 that has an aperture 190 therethrough, and a pivot pin 230 (FIGS. 6-7) insertable through the apertures 180,190 of the fork extensions 170 and pivot arm 220. As such, the pivot arm 220 is pivotable within the channel 200 about the pivot pin 230. In one embodiment, the pivot pin 230 includes an elastomeric ring 240 fixed within a circumferential channel 235 proximate one end 238 of the pivot pin 230. As such, when the pivot pin 230 is inserted into the aperture 180 of one of the fork extensions 170, the elastomeric ring 235 is compressed to retain the pivot pin 230 within the aperture 180 by friction.

As illustrated in the figures, the proximal portion 130 of the first joint 70 and the distal portion 140 of the second joint 100 each include the fork extensions 170, and the distal portion 140 of the first joint 70 and the proximal portion 130 of the second joint 100 include the pivot arm 220. In an alternate embodiment (not shown), the proximal portion 130 of the second joint 100 and the distal portion 140 of the first joint 70 may include the fork extensions 170 with the distal portion 140 of the second joint 100 and the proximal portion 130 of the first joint 70 each including the pivot arm 220. In yet another embodiment (not shown), the proximal portion 130 of the first and second joints 70,100 each include the fork extensions 170 while the distal portions of the first and second joint 70,100 each include the pivot arm 200. In yet another embodiment (not shown), the proximal portion 130 of the first and second joints 70,100 each include the pivot arm 220 while the distal portions of the first and second joint 70,100 each include the fork extensions 170.

Figure 3:
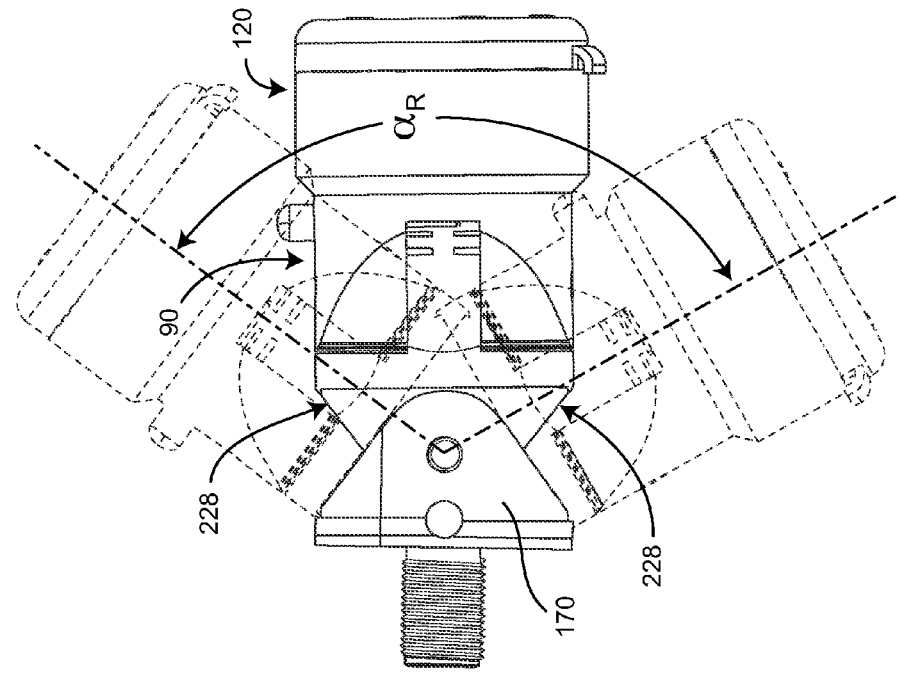
FIG. 3 is a left-side elevational view of the invention.
Figure 5:
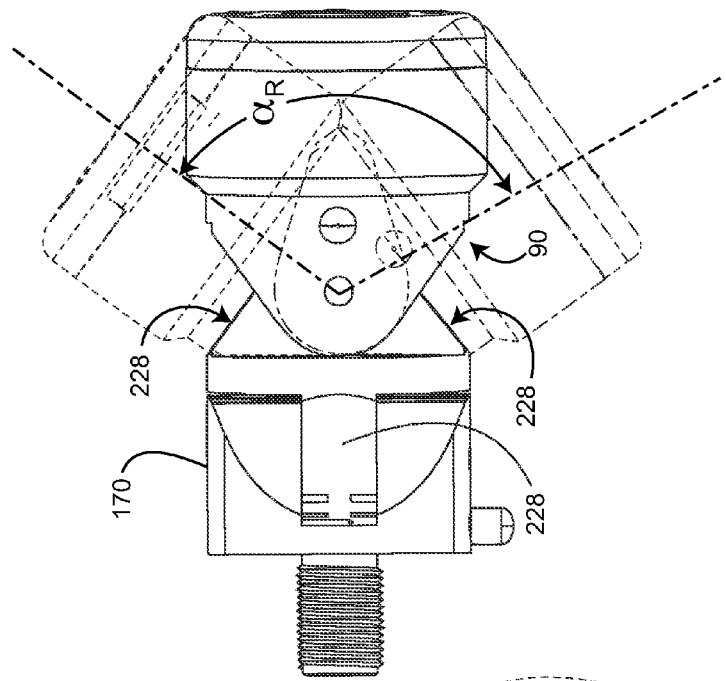
FIG. 5 is a top plan view of the invention.

In one embodiment, opposing sides of a peripheral surface 225 of each pivot arm 220 include a stop surface 228. The stop surfaces 228 form an angle $\theta$ therebetween of less than 90 degrees, each stop surface 228 adapted to contact the floor 210 of the channel 200 (FIGS. 3 and 5).

Each lock mechanism 160 of each joint 70,100 may include a plurality of partially-transverse grooves 250 in the peripheral surface 225 of each pivot arm 220, and a locking pin 260 that has a flat portion 270 that is adapted to lie flush with the floor 210 of the channel 200. The flat portion 270 has a locking protrusion 280 adapted to fit into any of the grooves 250 of the pivot arm 220. A spring 290 urges the locking protrusion 280 towards the pivot arm 220. The locking pin 260 includes an actuator portion 3100 protruding away from the fork extension 170 such that the actuator portion 300 may be depressed towards the fork extension 170 to retract the locking protrusion 280 away from the pivot arm 220, allowing the pivot arm 220 to rotate about the pivot pin 230. As such the actuator portion 300, which may be rounded for comfort, acts as a momentary actuator with the joint 70,100 being normally in a locked angular position. The actuator portion 300 of the locking pin 260 preferably projects through a locking aperture 340 that completely traverses one of the fork extensions 170 and only partially traverses the other fork extension 170. AS such the spring 290 is retained within the locking aperture 340 by the locking pin 260, and the locking pin 260 is in tern retained within the locking aperture 340 by the pivot arm 220 contacting the locking protrusion 280.

In one embodiment, each pivot arm 220 includes five such partially-transverse grooves 250. In another embodiment, each pivot arm 220 includes five pairs 310 of opposing partially-transverse grooves 250, such that the pivot arm 220 may be fixed with the fork extensions 170 in either a first orientation 320 or a second orientation 330 that is 180 degrees rotated from the first orientation 320 (FIG. 2). This makes assembly of the prosthetic wrist 10 easier after disassembly and cleaning, for example, as well as allowing the distal section 90 to be placed onto the central section 60 in such a way that the actuator portion 300 of the locking pin 260 is easiest to reach.

In one embodiment, the terminal device attachment mechanism 120 includes a terminal device socket 350 and a locking plate 360 that includes an aperture 370 that is alignable with the terminal device socket 350 when a locking plate actuator 390 is depressed against a locking plate biasing spring 380 (FIG. 6). Clearly other types of terminal device attachment mechanisms 120 may be utilized based on the type of terminal device 30 that is being utilized.

In use, with the wrist 10 attached to the arm prosthesis attachment socket 20 at the attachment post 50, and with the terminal device 30 attached to the terminal device attachment mechanism 120, the angle $\alpha$ between the proximal section 40 and the central section 60 may be manually set along the first pivot axis 80, and the angle $\beta$ between the central section 60 and the distal section 90 may be manually set along the second pivot axis 110.

While a particular form of the invention has been illustrated and described, it will be apparent that various modifications can be made without departing from the spirit and scope of the invention. For example, The specific shape of the fork extensions 170 may be modified, as well as the shape of each pivot arm 220. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A prosthetic wrist for attaching between an arm prosthesis attachment socket and a terminal device, comprising:
    a proximal section having at a proximal end thereof an attachment post adapted for selective attachment with the prosthesis attachment socket;
    a central section pivotally attached to the proximal section with a first joint, the first joint including a first pivot axis;
    a distal section pivotally attached to the central section with a second joint, the second joint including a second pivot axis substantially orthogonal to and non-intersecting with the first pivot axis, the distal section further including at a distal end thereof a terminal device attachment mechanism;
    the first and second joints each including a proximal portion, a distal portion, a pivot, and a lock mechanism adapted for allowing angular selection between the proximal and distal portions and locking thereof;
    the first and second joints each further including a pair of fork extensions each having a mutually aligned aperture therethrough and defining a channel therebetween with a floor, a pivot arm having an aperture therethrough, and a pivot pin insertable through the apertures of the fork extensions and pivot arm; and
    the pivot pin further including an elastomeric ring fixed within a circumferential channel proximate one end thereof;
    whereby with the wrist attached to the arm prosthesis attachment socket at the attachment post, and with a terminal device attached to the terminal device attachment mechanism, the angle between the proximal section and the central section may be manually set along the first pivot axis, and the angle between the central section and the distal section may be manually set along the second pivot axis, and whereby the pivot arm is pivotable within the channel of the fork about the pivot pin, and whereby when the pivot pin is inserted into the aperture of one of the fork extensions, the elastomeric ring is compressed to retain the pivot pin within the aperture by friction.

2. The prosthetic wrist of claim 1 wherein the attachment post includes a thread for engagement with a threaded arm prosthesis attachment socket.

3. The prosthetic wrist of claim 1 wherein the proximal portion of the first joint and the distal portion of the second joint include the fork extensions, and wherein the distal portion of the first joint and the proximal portion of the second joint include the pivot arm.

4. The prosthetic wrist of claim 1 wherein the proximal portion of the second joint and the distal portion of the first joint include the fork extensions, and wherein the distal portion of the second joint and the proximal portion of the first joint each include the pivot arm.

5. The prosthetic wrist of claim 1 wherein the proximal portion of the first joint and the proximal portion of the second joint include the fork extensions, and wherein the distal portion of the first joint and the distal portion of the second joint include the pivot arm.

6. The prosthetic wrist of claim 1 wherein the distal portion of the first joint and the distal portion of the second joint include the fork extensions, and wherein the proximal portion of the first joint and the proximal portion of the second joint include the pivot arm.

7. The prosthetic wrist of claim 1 wherein opposing sides of a peripheral surface of each pivot arm each include a stop surface, the stop surfaces forming an angle therebetween of less than 90 degrees, each stop surface adapted to contact the floor of the channel.

8. A prosthetic wrist for attaching between an arm prosthesis attachment socket and a terminal device, comprising:
    a proximal section having at a proximal end thereof an attachment post adapted for selective attachment with the prosthesis attachment socket;
    a central section pivotally attached to the proximal section with a first joint, the first joint including a first pivot axis;
    a distal section pivotally attached to the central section with a second joint, the second joint including a second pivot axis substantially orthogonal to and non-intersecting with the first pivot axis, the distal section further including at a distal end thereof a terminal device attachment mechanism;
    the first and second joints each including a proximal portion, a distal portion, a pivot, and a lock mechanism adapted for allowing angular selection between the proximal and distal portions and locking thereof;

the first and second joints each further including a pair of fork extensions each having a mutually aligned aperture therethrough and defining a channel therebetween with a floor, a pivot arm having an aperture therethrough, and a pivot pin insertable through the apertures of the fork extensions and pivot arm; and the lock mechanism of each joint including a plurality of partially-transverse grooves in the peripheral surface of each pivot arm, and a locking pin having a flat portion adapted to lie flush with the floor of the channel, the flat portion having a locking protrusion adapted to fit into any of the grooves of the pivot arm, a spring urging the locking protrusion towards the pivot arm, the locking pin including an actuator portion protruding away from the fork extension;

whereby with the wrist attached to the arm prosthesis attachment socket at the attachment post, and with a terminal device attached to the terminal device attachment mechanism, the angle between the proximal section and the central section may be manually set along the first pivot axis, and the angle between the central section and the distal section may be manually set along the second pivot axis, and whereby the pivot arm is pivotable within the channel of the fork about the pivot pin, and whereby the actuator portion may be depressed towards the fork extension to retract the locking protrusion from away from the pivot arm, allowing the pivot arm to rotate about the pivot pin.

9. The prosthetic wrist of claim 8 wherein each pivot arm includes six or fewer partially-transverse grooves on one side of the pivot arm.

10. The prosthetic wrist of claim 8 wherein each pivot arm includes six or fewer pairs of opposing partially-transverse grooves, whereby the pivot arm may be fixed with the fork in either of a first orientation or a second orientation 180 degrees rotated from the first orientation.

11. The prosthetic wrist of claim 8 wherein the actuator portion of the locking pin projects through a locking aperture that completely traverses one of the fork extensions and partially traverses the other fork extension, the spring being retained within the locking aperture by the locking pin, and the locking pin in turn being retained within the locking aperture by the pivot arm contacting the locking protrusion.

12. The prosthetic wrist of claim 1 wherein the terminal device attachment mechanism includes a terminal device socket and a locking plate that includes an aperture alignable with the terminal device socket when a locking plate actuator is depressed against a locking plate biasing spring.

* * * * *